Feb. 18, 1958 E. NEUMANN Plant Pat. 1,685
RED DESSERT APPLE TREE
Filed Jan. 31, 1955
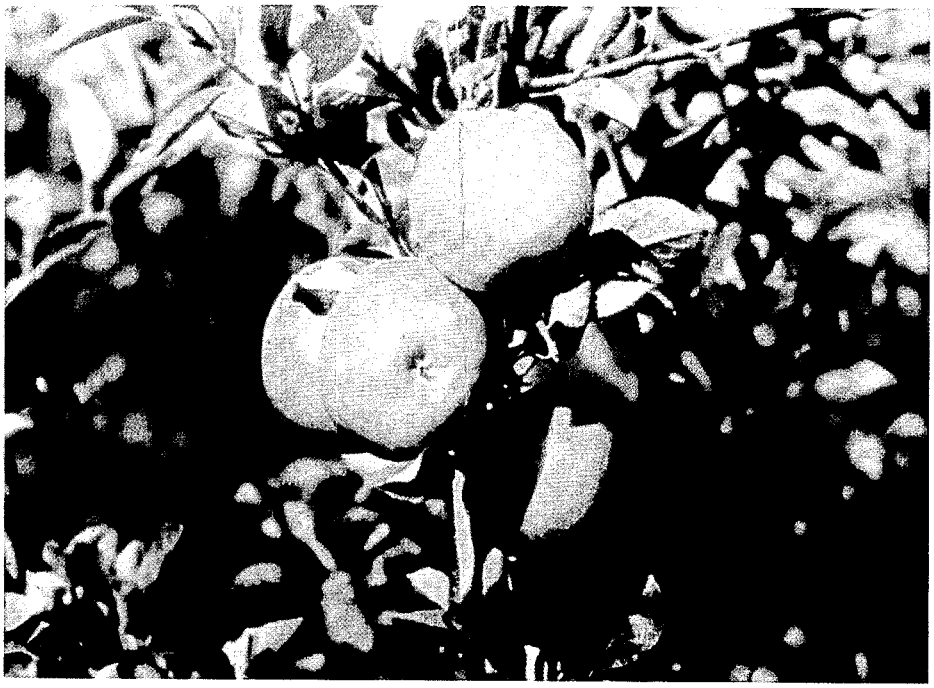
ERICH NEUMANN
INVENTOR
By Richardson, Davis and Morton
his ATT'YS.

United States Patent Office

Plant Pat. 1,685
Patented Feb. 18, 1958

1,685

RED DESSERT APPLE TREE

Erich Neumann, Zieverich, near Bergheim Lenft, Germany, assignor to Wilhelm Fey, Meckenheim, Germany Application January 31, 1955, Serial No. 491,551

1 Claim. (Cl. 47—62)

The present invention relates to a novel variety of apple tree which is identical in appearance with the James Grieve apple tree, the novel variety bearing apples identical with the James Grieve apples except for differences in color.

The James Grieve variety of apple tree has been known for about 60 or 70 years and is not covered by patent. The apples are dessert or eating apples having a skin predominantly greenish yellow in color with a minor amount of red coloration near the stem. The flavor and other characteristics of the pulp of the James Grieve variety make it a particularly desirable dessert apple, but the greenish yellow color of its skin renders it unattractive in appearance.

The instant variety was discovered as a mutation of the James Grieve variety, which mutation was highly colored. The mutation was then propagated asexually by grafting onto dwarf stock at Vorst bei Krefeld, Niederrhein, Federal Republic of Germany.

The following brief description of the novel variety of apple tree is given:

*Tree.*—Tall with a dark colored bark; growth is vigorous.

*Stem.*—Moderately long, knobbed at end, in a deep rather narrow cavity.

*Leaves.*—Rather long, dark green in color, very finely crenate and leather-like in quality.

*Blossoms.*—Light pink in color and bloom early.

*Fruit.*—Ripen in September to October. They are medium to large in size, being round and conical, about 3 inches wide and slightly longer. The eyes are closed in a rather deep even basin, of which the sides are a little plaited. The apples are identical in all respects with James Grieve apples except for their color which is approximately between Delft Rose .20 and Claret Rose .21 according to the British Horticultural Color Chart II, although the color may vary slightly depending upon the sun's rays. Each apple is substantially uniform in color.

Because of their shape, the apples pack easily in a minimum amount of space and their taste is the same as that of the James Grieve variety.

What is claimed is:

The new variety of apple tree substantially as shown and described, the new variety being identical with the James Grieve variety except for the fruit which in color is approximately between Delft Rose .20 and Claret Rose .21.

No references cited.